(12) United States Patent
Thomas et al.

(10) Patent No.: US 6,786,667 B1
(45) Date of Patent: Sep. 7, 2004

(54) APPLICATOR FOR APPLYING NAIL POLISH REMOVER

(76) Inventors: Angela M. Thomas, 31 Passaic Ct., Richmond Hill, GA (US) 31324; Mark A. Thomas, 31 Passaic Ct., Richmond Hill, GA (US) 31324

( * ) Notice: Subject to any disclaimer, the term of this patent is extended or adjusted under 35 U.S.C. 154(b) by 0 days.

(21) Appl. No.: 10/756,967

(22) Filed: Jan. 15, 2004

(51) Int. Cl.[7] .............................. B43K 5/14; B43K 5/00
(52) U.S. Cl. ..................... 401/134; 401/133; 401/205
(58) Field of Search ........................... 401/132–135, 401/196–205; 604/3; 222/541.2

(56) References Cited

U.S. PATENT DOCUMENTS

| | | |
|---|---|---|
| 1,007,816 A | 11/1911 | Stubenrauch |
| D92,088 S | 4/1934 | Johnson |
| D137,554 S | 3/1944 | Herb |
| D140,549 S | 3/1945 | Magann |
| 3,759,259 A * | 9/1973 | Truhan ........................... 604/3 |
| 4,454,622 A | 6/1984 | Poppendieck |
| 4,884,913 A | 12/1989 | Smith et al. |
| 4,925,327 A * | 5/1990 | Wirt ........................... 401/205 |
| 4,932,802 A * | 6/1990 | Cantone ....................... 401/17 |
| 5,938,363 A * | 8/1999 | Timms et al. ............... 401/209 |
| 6,505,985 B1 * | 1/2003 | Hidle et al. ................. 401/134 |

* cited by examiner

*Primary Examiner*—David J. Walczak
(74) *Attorney, Agent, or Firm*—Donald R. Schoonover

(57) ABSTRACT

A single-use applicator contains nail polish remover and an applicator element. A liquid conduit has one end fluidically connected to the applicator element and a point on another end. The nail polish remover is liquid and is contained in a container having a puncturable cover that is located adjacent to the point of the conduit. The applicator element is located in one unit and the liquid is located in a second unit. The two units are threadably connected and when screwed together, the point punctures the cover and fluidically connects the liquid nail polish remover to the applicator element. The applicator is used in the manner of a writing instrument to remove nail polish.

2 Claims, 1 Drawing Sheet

APPLICATOR FOR APPLYING NAIL POLISH REMOVER

BACKGROUND OF THE INVENTION

1. Field of the Invention

The present invention relates to the general art of toiletry devices, and to the particular field of nail devices with fluent material.

2. Discussion of the Related Art

Many women apply nail polish to their fingernails and to their toenails. This process is generally carried out using a nail polish applicator brush and a bottle containing the nail polish. There are many examples of such brush/bottle combinations in the art.

However, to remove nail polish, a person must apply a nail polish remover, such as acetone or the like, to the polished nail. This is often done by pouring the nail polish remover from a container onto a cotton pad and then using the soaked cotton pad to remove the nail polish by applying the soaked cotton pad to the polished nail. This can be messy, cumbersome, inefficient and onerous. The cotton pad can be dropped, or the liquid can spill from the container onto the user, or the liquid can be applied to the user's skin by an over-large cotton pad. It is not desirable to have nail polish remover applied to any surface except the nail polish to be removed. Certainly it is not desirable to have nail polish remover applied to a user's skin.

Therefore, there is a need for an applicator system for neatly and efficiently applying nail polish remover to nail polish.

Still further, most nail polish removers, including acetone, are quite volatile and will evaporate if the container is not securely closed between uses. Such evaporation is wasteful and the fumes associated with such evaporation may not be desirable.

Therefore, there is a need for an applicator system for applying nail polish remover that will make efficient use of the liquid nail polish remover and will conserve the liquid when the applicator is not in use.

Since cotton balls are generally manufactured for a multitude of uses, these items are often too large for efficient use to apply nail polish remover to a user's nails. Thus, nail polish remover is often wasted during the saturation of a cotton ball for use. The large cotton ball then may undesirably apply the nail polish remover to the user's skin in addition to applying the remover to the nail polish. While this is undesirable in any instance, it is especially undesirable if a person is a nail specialist and is applying the polish and polish remover to others, often many times a day. The repeated application of nail polish remover to such a person's skin is not desirable.

Therefore, there is a need for an applicator system for applying nail polish remover that will make efficient use of any applicator element and will locate and size the applicator element to make efficient use of the liquid nail polish remover and to help prevent the applicator element from contacting a user's skin.

Still further, many women wish to remove some or all of their nail polish while they are traveling or are otherwise away from home. These women must purchase the nail polish remover and then discard any unused portion of that remover after use. This may be expensive and inconvenient. However, carrying containers of liquid nail polish remover while traveling is often not convenient.

Therefore, there is a need for an applicator system for applying nail polish remover that can be conveniently stored and used while traveling.

Sometimes, while applying nail polish remover, a user will drop the container or the applicator element. This is not desirable since the nail polish remover liquid may damage a surface which is contacted.

Therefore, there is a need for an applicator system for applying nail polish remover that can be securely held while the nail polish remover is being applied.

PRINCIPAL OBJECTS OF THE INVENTION

It is a main object of the present invention to provide an applicator system for neatly and efficiently applying nail polish remover to nail polish.

It is another object of the present invention to provide an applicator system for applying nail polish remover that will make efficient use of the liquid nail polish remover and will conserve the liquid when the applicator is not in use.

It is another object of the present invention to provide an applicator system for applying nail polish remover that will make efficient use of any applicator element and will locate and size the applicator element to make efficient use of the liquid nail polish remover and to help prevent the applicator element from contacting a user's skin.

It is another object of the present invention to provide an applicator system for applying nail polish remover that can be conveniently stored and used while traveling.

It is another object of the present invention to provide an applicator system for applying nail polish remover that can be securely held while the nail polish remover is being applied.

SUMMARY OF THE INVENTION

These, and other, objects are achieved by an applicator for applying nail polish remover which comprises a liquid container unit which includes a chamber containing liquid nail polish remover; a puncturable foil cover on the chamber; an applicator unit which includes an applicator element; a fluid conduit which has a pointed end located adjacent to the puncturable foil, and a dispensing end in fluid connection with the applicator element; and a screw thread connection between the liquid container unit and the applicator unit, the screw thread connection movably connecting the applicator unit to the liquid container unit so the applicator element moves between a stored position and a use position with respect to the liquid container unit, the fluid conduit moving from adjacent to the puncturable foil and puncturing the puncturable foil and moving into the chamber of the liquid container unit as the applicator unit is moved from the stored position into the use position, the fluid conduit fluidically connecting the nail polish remover in the chamber in the liquid container unit with the applicator element in the applicator unit when the applicator unit is in the use position.

The applicator system embodying the present invention thus will remain sealed until needed thereby conserving the liquid and protecting it from accidental spilling. The applicator system of the present invention also will apply nail polish remover in very precise amounts and in a very precise manner so very little, if any, nail polish remover is applied to any area other than directly to the nail polish being removed. This protects the skin of the user as well as conserves the nail polish remover. The applicator of the present invention is sealed when it is not in use and thus can be carried in a purse or any other handbag without danger of the liquid spilling. The amount of nail polish remover in a single applicator can be precisely metered to remove nail polish from a specific number of nails, for example, five to ten, whereby there will be no wasted liquid. This will be economical and conservative of the liquid. The container can be securely held so there is little, if any, danger of dropping the container and accidentally applying the liquid nail polish remover to a surface that may be damaged by that liquid.

BRIEF DESCRIPTION OF THE DRAWING FIGURES

DETAILED DESCRIPTION OF THE PREFERRED EMBODIMENT

Figure 2:
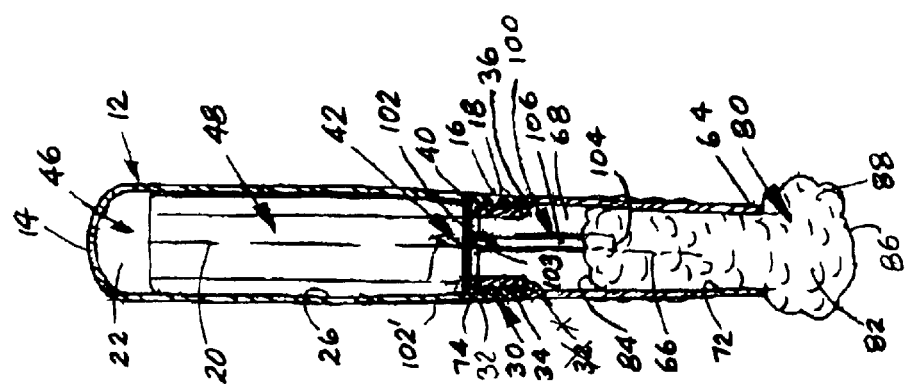
FIG. 2 is an elevational, partially cross-sectional view of the applicator system shown in FIG. 1 taken along line 2—2 of FIG. 1.
Figure 1:
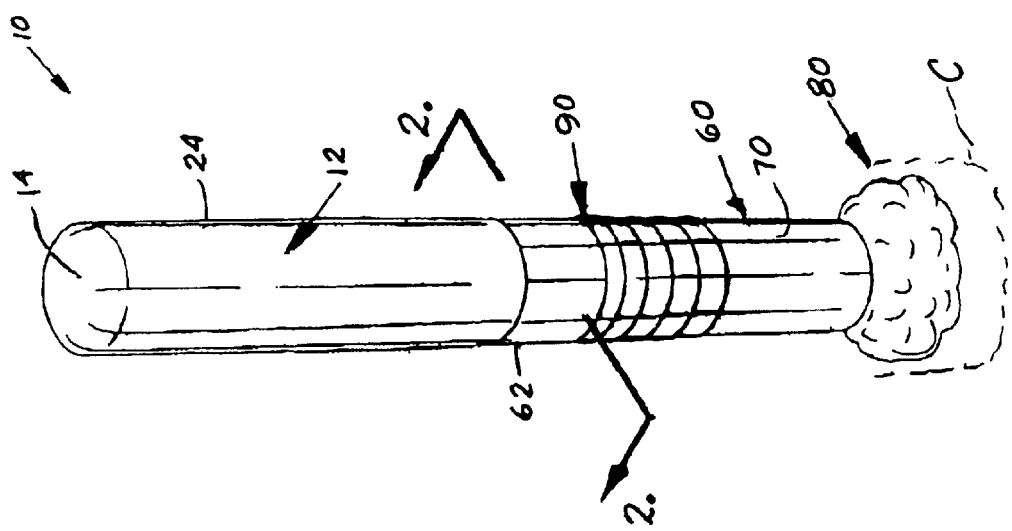
FIG. 1 is a perspective view of an applicator system for applying nail polish remover embodying the present invention.

Other objects, features and advantages of the invention will become apparent from a consideration of the following detailed description and the accompanying drawings.

Referring to the figures, it can be understood that the present invention is embodied in an applicator 10 for efficiently and precisely applying exact amounts of nail polish remover to a user's nails without contacting the user's skin. Applicator 10 comprises a liquid container unit 12 which includes a closed end 14, an open end 16 having a rim 18, and a longitudinal axis 20 which extends between the closed end 14 and the open end 16.

A blind-ended bore 22 is defined between the open end 16 and the closed end 14.

Unit 12 further includes an outer surface 24 and an inner surface 26 adjacent to the blind-ended bore 22. An annular shoulder 30 is mounted on the inner surface 26 adjacent to the open end 16, and includes a first rim 32 that is positioned to be located beyond the rim 18 of the open end 16 in the direction of the longitudinal axis 20 of the liquid container unit 12, an outer surface 34 on the annular shoulder 30, and a second rim 36 that is spaced apart from the first rim 32 in the direction of the longitudinal axis 20 of the liquid container unit 12. The outer surface 34 of the annular shoulder 30 is located between the rim 18 of the open end 16 of the liquid container unit 12 and the second rim 36 of the annular shoulder 30.

An external screw thread 40 is located on the outer surface 34 of the annular shoulder 30.

A puncturable foil 42 is mounted on the first rim 32 of the annular shoulder 30 and extends across the open end 16 of the liquid container unit 12 to close the blind-ended bore 22 adjacent to the open end 16 of the liquid container unit 12.

A chamber 46 is defined in the liquid container unit 12 by the inner surface 26 adjacent to the blind-ended bore 22 and the puncturable foil 42.

Nail polish remover liquid 48, such as acetone or the like, is contained in the chamber 46 when the liquid container unit 12 is in a stored condition, such as shown in FIG. 2.

An applicator unit 60 is movably attached to the liquid container unit 12 and includes a first open end 62, a second open end 64, and a longitudinal axis 66 which extends between the first open end 62 of the applicator unit 60 and the second open end 64 of the applicator unit 60. The longitudinal axis 66 of the applicator unit 60 is co-linear with the longitudinal axis 20 of the liquid container unit 12.

A through bore 68 extends between the first open end 62 of the applicator unit 60 and the second open end 64 of the applicator unit 60. Unit 60 includes an outer surface 70 and an inner surface 72 adjacent to the through bore 68.

A screw thread 74 is located on the inner surface 72 of the applicator unit 60 adjacent to the first open end 62 of the applicator unit 60. The screw thread 74 of the applicator unit 60 is sized and shaped to threadably engage the external screw thread 40 on the outer surface 34 of the annular shoulder 30 of the liquid container unit 12 and threadably attaches the applicator unit 60 to the liquid container unit 12. The applicator unit 60 moves toward and away from the liquid container unit 12 as the applicator unit 60 is displaced to move the screw threads 74 of the applicator unit 60 with respect to the external screw thread 40 on the outer surface 34 of the annular shoulder 30 of the liquid container unit 12. The applicator unit 60 moves between a stored position and a use position, with the use position being closer to the open end 16 of the liquid container unit 12 than the stored position.

A nail polish remover applicator element 80 is mounted on the applicator unit 60. The nail polish remover applicator element 80 can be cotton and includes a body 82 that will absorb and wick nail polish remover liquid. Element 80 further includes a first end 84 that is located inside the through bore 68 of the applicator unit 60, a second end 86 that is spaced apart from the second open end 64 of the applicator unit 60 in the direction of the longitudinal axis 66 of the applicator unit 60, and a portion 88 that extends beyond the outer surface 70 of the applicator unit 60 adjacent to the second open end 64 of the applicator unit 60.

A plurality of grooves 90 are defined in the outer surface 70 of the applicator unit 60 to provide a secure gripping surface for the applicator 10 during use.

A fluid conduit 100 is located in the through bore 68 of the applicator unit 60. The fluid conduit 100 includes a pointed end 102 which is positioned to be in contact with the puncturable foil 42 mounted on the first rim 32 of the annular shoulder 30 of the liquid container unit 12 when the applicator unit 10 is in the stored position. The pointed end 102 punctures the puncturable foil 42 and moves into the chamber 46 in the liquid container unit 12 and into fluid contact with the nail polish remover liquid 48 contained in the chamber 46 when the applicator unit 60 is moved into the use position. A dispensing end 104 of the fluid conduit 100 is fluidically connected to the applicator element and is securely mounted on the applicator element so that the fluid conduit 100 will move with the applicator unit 60 between the stored position and the use position and will be mounted securely enough to puncture the puncturable foil 42.

A through bore 106 extends between the pointed end 102 of the fluid conduit 100 and the dispensing end 104 of the fluid conduit 100 and fluidically connects the pointed end 102 of the fluid conduit 100 to the dispensing end 104 of the fluid conduit 100 to convey liquid nail polish remover 48 from the chamber 46 in the liquid container unit to the applicator element in the applicator unit when the applicator unit is in the use position.

Applicator 10 is used by simply screwing the applicator unit 60 towards the liquid container unit 12 until the fluid conduit 100 punctures the puncturable foil 42 and liquid nail polish remover 48 flows through the conduit 100 into the applicator element. As soon as the applicator element is sufficiently saturated with nail polish remover, applicator 10 can be used in the manner of a writing instrument, such as a pen or the like, to place the applicator element in contact with the nail polish to be removed. Applicator 10 is disposable and will contain enough nail polish remover to remove the polish from five to ten nails. It is noted that FIG. 2 shows the applicator unit in an intermediate position between the stored position and the use position as the pointed end 102 is moving through the puncturable foil 42. Dotted line 102' indicates the use position of the pointed end 102 and dotted line 103 indicated the stored position of the pointed end 102. No cap is needed since there is no liquid in the applicator element until the applicator element is used. However, if desired, a cap, indicated in dotted lines by cap C, may be used if desired to ensure against accidental dispensing of the nail polish should the applicator be accidentally contacted in a manner that punctures the foil, and to protect against such accidental movement of the fluid conduit. The applicator can be sold on blister packages or in other packages so it can be conveniently stored.

It is understood that while certain forms of the present invention have been illustrated and described herein, it is not to be limited to the specific forms or arrangements of parts described and shown.

What is claimed is:

1. An applicator for applying nail polish remover comprising:
   a) a liquid container unit which includes
      (1) a closed end,
      (2) an open end having a rim,
      (3) a longitudinal axis extending between the closed end and the open end,
      (4) a blind-ended bore defined between the open end and the closed end,
      (5) an outer surface,
      (6) an inner surface adjacent to the blind-ended bore,
      (7) an annular shoulder mounted on the inner surface adjacent to the open end, the annular shoulder including a first rim that is positioned to be located beyond the rim on the open end in the direction of the longitudinal axis of said liquid container unit, an outer surface on the annular shoulder and a second rim spaced apart from the first rim in the direction of the longitudinal axis of said liquid container unit, the outer surface of the annular shoulder being located between the rim of the open end of said liquid container unit and the second rim of the annular shoulder,
      (8) an external screw thread on the outer surface of the annular shoulder,
      (9) puncturable foil mounted on the first rim of the annular shoulder and which extends across the open end of said liquid container unit to close the blind-ended bore adjacent to the open end of said liquid container unit,
      (10) a chamber defined in said liquid container unit by the inner surface adjacent to the blind-ended bore and the puncturable foil, and
      (11) nail polish remover liquid contained in the chamber when said liquid container unit is in a stored condition;
   b) an applicator unit which is movably attached to said liquid container unit and which includes
      (1) a first open end,
      (2) a second open end,
      (3) a longitudinal axis extending between the first open end of said applicator unit and the second open end of said applicator unit, the longitudinal axis of said applicator unit being co-linear with the longitudinal axis of said liquid container unit,
      (4) a through bore extending between the first open end of said applicator unit and the second open end of said applicator unit,
      (5) an outer surface,
      (6) an inner surface adjacent to the through bore,
      (7) a screw thread on the inner surface of said applicator unit adjacent to the first open end of said applicator unit, the screw thread of said applicator unit being sized and shaped to threadably engage the external screw thread on the outer surface of the annular shoulder of said liquid container unit and threadably attach said applicator unit to said liquid container unit, said applicator unit moving toward and away from said liquid container unit as said applicator unit is moved to move the screw threads of said applicator unit with respect to the external screw thread on the outer surface of the annular shoulder of said liquid container unit, the applicator unit moving between a stored position and a use position, with the use position being closer to the open end of said liquid container unit than the stored position,
      (8) a nail polish remover applicator element mounted on said applicator unit, the nail polish remover applicator element including
         (A) a body that will absorb and wick nail polish remover liquid,
         (B) a first end located inside the through bore of said applicator unit,
         (C) a second end which is spaced apart from the second open end of said applicator unit in the direction of the longitudinal axis of said applicator unit, and
         (D) a portion that extends beyond the outer surface of said applicator unit adjacent to the second open end of said applicator unit, and
      (9) a plurality of grooves defined in the outer surface of said applicator unit; and
   c) a fluid conduit located in the through bore of said applicator unit, said fluid conduit including
      (1) a pointed end which is positioned to be in contact with the puncturable foil mounted on the first rim of the annular shoulder of said liquid container unit when said applicator unit is in the stored position, the pointed end puncturing the puncturable foil and moving into the chamber in said liquid container unit and into fluid contact with the nail polish remover liquid contained in the chamber when the applicator unit is moved into the use position,
      (2) a dispensing end fluidically connected to the applicator element, and
      (3) a through bore extending between the pointed end of said fluid conduit and the dispensing end of said fluid conduit and fluidically connecting the pointed end of said fluid conduit to the dispensing end of said fluid conduit to conduct liquid nail polish remover from the chamber in said liquid container unit to the applicator element in said applicator unit when said applicator unit is in the use position.

2. The applicator as described in claim 1 wherein the liquid nail polish remover is acetone.

* * * * *